United States Patent
Hein et al.

(10) Patent No.: US 7,075,894 B2
(45) Date of Patent: Jul. 11, 2006

(54) ALGORITHM FOR PRIORITIZATION OF EVENT DATUM IN GENERIC ASYNCHRONOUS TELEMETRIC STREAMS

(75) Inventors: Trent R. Hein, Boulder, CO (US); Ned McClain, Boulder, CO (US)

(73) Assignee: Fair Isaac Corporation, Minneapolis, MN (US)

( * ) Notice: Subject to any disclaimer, the term of this patent is extended or adjusted under 35 U.S.C. 154(b) by 1179 days.

(21) Appl. No.: 09/809,332

(22) Filed: Mar. 14, 2001

(65) Prior Publication Data

US 2002/0178275 A1   Nov. 28, 2002

(51) Int. Cl.
*H04J 1/16*   (2006.01)

(52) U.S. Cl. .................................................... 370/244

(58) Field of Classification Search ............... 706/50; 709/224; 707/1, 102, 103; 340/825.07; 345/200.33, 200.54, 200.58; 370/389, 241, 370/252, 254
See application file for complete search history.

(56) References Cited

U.S. PATENT DOCUMENTS

| | | | |
|---|---|---|---|
| 5,781,703 A | 7/1998 | Desai et al. | |
| 5,905,868 A | 5/1999 | Baghai et al. | |
| 5,995,943 A | 11/1999 | Bull et al. | |
| 6,041,362 A | 3/2000 | Mears et al. | |
| 6,055,493 A | 4/2000 | Ries et al. | |
| 6,108,686 A | 8/2000 | Williams, Jr. | |
| 6,148,335 A | 11/2000 | Haggard et al. | |
| 6,289,332 B1 | 9/2001 | Menig et al. | |
| 6,292,828 B1 | 9/2001 | Williams | |
| 6,416,471 B1 * | 7/2002 | Kumar et al. | 600/300 |
| 6,426,948 B1 | 7/2002 | Bowman-Amuah | |
| 6,454,708 B1 * | 9/2002 | Ferguson et al. | 600/300 |

OTHER PUBLICATIONS

Copy of the International Search Report for PCT Application Serial No. PCT/US02/07211, mailed on Nov. 13, 2002.

* cited by examiner

*Primary Examiner*—Dang Ton
(74) *Attorney, Agent, or Firm*—Glenn Patent Group; Michael A. Glenn (57) ABSTRACT

Systems, methods, and algorithms for prioritizing event datum received from a plurality of asynchronous telemetric streams. A historic learning algorithm is utilized to prioritize event datum based upon a current level of system health and historic correlations between event values and recorded levels of system health.

9 Claims, 4 Drawing Sheets

ALGORITHM FOR PRIORITIZATION OF EVENT DATUM IN GENERIC ASYNCHRONOUS TELEMETRIC STREAMS

BACKGROUND OF THE INVENTION

The present invention relates generally to systems and methods for monitoring and prioritizing event datum and, more particularly, to systems and methods for monitoring and prioritizing event datum in asynchronous telemetric streams.

Aggregating information from multiple live event streams is a challenge that appears in many modem event correlation environments. For example, when asynchronous events occur near simultaneously, it is often difficult to determine which event(s) should be given priority for delivery to a receiver and which events, if any, should be discarded.

Considerable research for handling event streams has been undertaken, but often such efforts have focused on environments such as a lab or collection array where prioritization is side-stepped in order to reduce implementation complexity. In environments such as medical monitoring or production application and system monitoring, it is often the case that events, which arrive asynchronously, may coincide and the traditional approach has relied upon traditional queuing theory such as first-in, first-out or round-robin. While these approaches are very utilitarian and functional in the vast majority of event stream environments, they fail to perform adequately in situations where the number of events arriving at a nexus vastly exceeds the number of events that can be forwarded by the nexus over a given time period. In some situations the nexus is limited by number or size of transactions it can forward, and in other situations it may be the user's choice to not forward (discard) lower priority events.

In view of the foregoing, it is believed that those skilled in the art would find systems, methods, and algorithms that could be used to monitor and/or prioritize asynchronous events in, for example, mission critical or fault tolerant environments to be quite useful. It is also believed that such systems, methods, and algorithms may be used to enhance overall user experiences and to reduce the risk that telemetry data may be misinterpreted.

SUMMARY OF THE INVENTION

In one innovative aspect, the present invention is directed to systems, methods, and algorithms for monitoring and prioritizing event datum in asynchronous telemetric streams. In an exemplary embodiment, an algorithm in accordance with the present invention may employ a "historic learning" capability to prioritize event datum obtained from separate streams.

In one preferred embodiment, this is done by defining a threat level (TL) that provides an indication of overall system health, developing tables to track relationships between threat levels (TLs) and event values, and/or changes in event values, that may be exhibited over time, and using the identified relationships to predict the effect that a current event may have on overall system health at any given point in time.

In another embodiment, weighting factors may be applied to the factors considered by an algorithm in accordance with the present invention to enable the algorithm to more accurately assess the likely effect of a particular event upon overall system health.

In other innovative aspects, the present invention is directed to event monitoring systems that may be used, for example, within medical establishments, production facilities, service networks, and information technology management systems to prioritize events and thereby enhance the probability that a response to an event will be made in a timely manner and with a higher degree of effectiveness than would be possible using conventional technologies.

In view of the foregoing, it is an object of the present invention to provide improved systems, methods, and algorithms for use in monitoring and prioritizing event datum in asynchronous telemetric streams.

BRIEF DESCRIPTION OF THE DRAWINGS

Various objects and advantages and a more complete understanding of the present invention will be apparent and more readily appreciated by reference to the following Detailed Description and to the appended claims when taken in conjunction with the accompanying Drawings wherein:

DETAILED DESCRIPTION

Turning now to the drawings, in one innovative aspect, the present invention is directed to systems, methods, and algorithms for prioritizing event datum in asynchronous telemetric streams or, alternatively, improving predictability of event forwarding when the number of events arriving at a nexus exceeds the number of events that can be forwarded by the nexus over a given period of time.

In one exemplary embodiment, the systems, methods, and algorithms of the present invention will be discussed within the context of a system monitoring environment where multiple agents collect quantitative metrics about various aspects of the system—such as performance, load, and errors. Some of the events may indicate a problem that requires a response, and some events may be purely informational. At any given time, the number of event notifications may exceed an "upstream" event handling capability of the system—such as a graphical user interface that is accessible only over low bandwidth link, or perhaps limited by processing power. Although this exemplary environment discussed herein has been chosen because of the challenges it presents, those skilled in the art will appreciate that the systems, methods, and algorithms described herein are extensible to other similar event forwarding environments.

One of the primary challenges of prioritizing events within the environment described herein is that very little information is available about what the events in the data stream truly represent. In a typical system monitoring environment, a flag is forwarded indicating whether or not an event notification represents an alarm condition, but beyond that the behavior and interrelationship (which may range from completely unrelated to highly related) between streams is opaque, hence a generic handling algorithm is necessary. In addition, the typical system-monitoring environment is resource constrained in the sense that it should be capable of handling an arbitrary number of streams without requiring significant processor or memory resources for each additional stream. While these environmental conditions are extremely limiting in terms of algorithmic flexibility, they are typical for a number of event correlation and reporting environments, hence the systems, methods, and algorithms described herein have been specifically designed to thrive in this setting. Specifically, in a preferred embodiment, an algorithm in accordance with the present invention will exhibit O(n) behavior with respect to incremental resources required for additional streams.

As used in the following examples, the term "system" represents a set of data streams that arrive at a single forwarding nexus. Examining all of the streams of a system and determining whether they're currently "in alarm" (alarm flag is set on arriving events) provides an indication or measure of the "health" of the overall system. Stated somewhat differently, where fewer streams are in alarm, system health is deemed to be better. Accordingly, in one preferred form, an algorithm in accordance with the present invention will include a variable, referred to herein as a Threat Level (TL), that represents the health level (or lack thereof) of the system. Since TL preferably is calculated based upon the alarm status of each stream received at a nexus, reliance is placed upon the senders (parties forwarding events to the stream) within a system to correctly set this condition flag. Those skilled in the art will appreciate that, in environments where this is not already done, it is a relatively simple exercise to write a function that sets an alarm status based on a current stream condition. In one preferred embodiment, the variable TL is defined as follows:

Definition: At a given time t, the TL value of the system is:

TL=percentage of streams in alarm state (range is 0 to 100)

Hence, a low TL infers a healthy system, and a high TL infers an unhealthy system. As will be discussed in more detail below, as individual streams experience various conditions, historic values of the variable TL may be used to help prioritize future events.

Those skilled in the art will appreciate that the variable TL should be recalculated for every time period t in order to provide for the most accurate prioritization, but depending upon the degree of accuracy required by a given system, the recalculation may be performed on a less frequent basis.

An algorithm in accordance with the present invention also preferably takes into consideration the current value of the datum in a stream, the rate of change of that datum, and the effect of both values on TL. However, since a system typically will have neither control nor empirical understanding of the datum in the stream, an algorithm in accordance with the present invention preferably will normalize these values before they can be factored into the equation.

The variable NORM(V) is calculated using the historical MIN and MAX values for a stream. The MIN and MAX values are used to map the stream's values to a 0–100 scale, and the NORM(V) variable preferably is defined as follows:

Definition: At a given time t, NORM($V_t$) is:

NORM($V_t$)=($V_t$-MIN)×[100/(MAX-MIN)]

In a preferred embodiment, each time that a value is received, the historical MIN and MAX values will be checked to determine whether they are still valid.

An assumption based upon experience is that, in typical event correlation environments, a sequence of events that correlated to produce particular states in the past is highly likely to correlate to produce those states in the future. In more simple terms, if a system can determine what caused a problem in the past (e.g., in the last instance), the system can adjust to report it better in the future. For this reason, an algorithm in accordance with the present invention preferably provides for tracking of historic TL values as they relate to both the instantaneous normalized value of a stream (NORM($V_t$)) and the first derivative of this value (dNORM($V_t$)/dt). These values preferably are stored in lookup tables called the Instantaneous Value Influence Table (IVIT) and Differentiated Value Influence Table (DVIT), respectively. For each possible value of NORM($V_t$) (which has 101 possible values, ranging 0 to 100), the exponential average of TL at time t (EXPA($TA_t$)) also is stored. Likewise, for each possible value of dNORM($V_t$)/dt (which has 201 possible values, ranging from –100 to 100), EXPA($TA_t$) is stored.

In order to facilitate useful operation of the tables before they are populated with relevant data, the algorithm of the present invention preferably will first initializes each table. Initialization involves setting each EXPA($TA_t$) field to the worst possible value: 100. By initializing the tables to the worst possible values, it is possible to ensure that previously unseen normalized values and differentials will be prioritized as high as possible. As time progresses beyond initialization, the exponential average function will iteratively modify the EXPA($TA_t$) fields, and the initial value will quickly become insignificant.

In a preferred embodiment, an algorithm in accordance with the present invention will calculate the exponential average in a manner that is well known in the art, but for completeness the calculation is described in detail herein. In order to calculate the exponential average, the exponent must first be chosen. The choice of exponent is dependent on the number of periods desired in the consideration of the exponential average, and this varies based on application. Herein, the term "PERIOD" is used to represent the number of time periods in the calculation. Based on this, the exponent is calculated as:

EXP=2/(PERIOD+1)

Then, the exponential average can be calculated as follows:

Definition:

$$\text{EXPA}(TL_t) = (TL_i \times \text{EXP}) + \begin{pmatrix} CVIT[NORM(V_t)] \times (1 - \text{EXP}) \\ \text{or,} \\ DVIT[dNORM(V_t)/dt] \end{pmatrix}$$

As indicated above, a particularly innovative aspect of an algorithm in accordance with the present invention is the ability to prioritize event datum from asynchronous telemetric streams. In one preferred embodiment, an algorithm in accordance with the present invention will calculate the priority for a particular datum in an event stream, while taking into consideration each of the variables described above.

Thus, in a preferred embodiment, each of the variables listed in Table 1, below, will be used in a prioritization calculation.

TABLE 1

State maintained for each stream S.

| | |
|---|---|
| MIN | Running minimum sample of V |
| MAX | Running maximum sample of V |
| ALARM | Current alarm state (1 = in alarm, 0 = not in alarm) |
| NORM($V_{t-1}$) | Normalized value of S at time = t − 1 |
| IVIT(S) | Instantaneous Value Influence Table |
| DVIT(S) | Differentiated Value Influence Table |

Other variables that preferably will be used in performing a prioritization calculation are set forth in Table 2, below.

TABLE 2

Key variables and functions:

| | |
|---|---|
| $S_n$ | Data stream n |
| $V_t(S)$ | Value of stream S at time t |
| TL | Threat level for the system as a whole |
| NORM($V_t$) | Normalized value of S at time t |
| EXPA($TL_t$) | Exponential average of TL at time t |

In a preferred form, an algorithm in accordance with the present invention will combine the variables set forth in Tables 1 and 2 into a unified equation to calculate $P_S$, the priority rating of stream S at time t. This result has a possible range of 0 to 100, with the higher values representing a higher forwarding priority. This calculation is performed as follows:

Definition:

$$Ps = \left( \frac{IVIT(NORM(V_t)) + DVIT(dNORM(V_t)/dt)}{4} \right) + (ALARMs \times 50)$$

Using this equation, it is possible to make decisions based on which events should be forwarded, or in what order events should be forwarded, based on the value of $P_S$. In one presently preferred embodiment, streams currently in "alarm" state will be prioritized higher than streams not in alarm. However, it should be appreciated that "weighting factors" may be used to modify the above-described calculation such that control may be taken over alarm-related behavior.

In an alternative embodiment of the present invention, the prioritization calculation may be modified to assess how much of an effect a particular alarm state may have on overall system operation, system health, or the TL variable. Moreover, in some instances, it may be desirable to adjust how much of an effect alarm state has on priority. Exemplary, variables that may be used to represent weighting variables are set forth in Table 4, below.

TABLE 4

Relative Weights: Calculated Effects on TL/Alarm Flag

| | |
|---|---|
| $W_1$ | Weight of calculated priority versus alarm flag |
| $W_2$ | Weight of alarm flag versus calculated priority |
| | Where: $W_1 + W_2 = 2$ |

In one preferred embodiment, an algorithm in accordance with the present invention may utilize two different relative weighting variables. In addition to weighting alarm state versus calculated priority, an algorithm in accordance with the present invention may weight the relative influence of the IVIT versus the DVIT tables. Since the differential table generally produces more predictive, but less reliable prioritization than the integral table, a balance between the two is preferred. The following variables set forth in Table 5, below, preferably are used in the weighted stream prioritization equation, which follows the table.

TABLE 5

Relative Weights: IVIT/DVIT tables

| | |
|---|---|
| $W_3$ | Relative weight of IVIT with respect to DVIT |
| $W_4$ | Relative weight of DVIT with respect to IVIT |
| | Where: $W_3 + W_4 = 2$ |

$$Ps = W_1 \times \left( \frac{W_3 \times IVIT(NORM(V_t)) + W_4 \times DVIT(dNORM(V_t)/dt)}{4} \right) + W_2 \times (ALARMs \times 50)$$

Those skilled in the art will appreciate that weightings need not be fixed between iterations of the algorithm. An intelligent implementation preferably will adjust the weightings based on changes to IVIT and DVIT tables, instantaneous stream values and derivatives, alarm status, system TL, and other relevant data.

Figure 1:
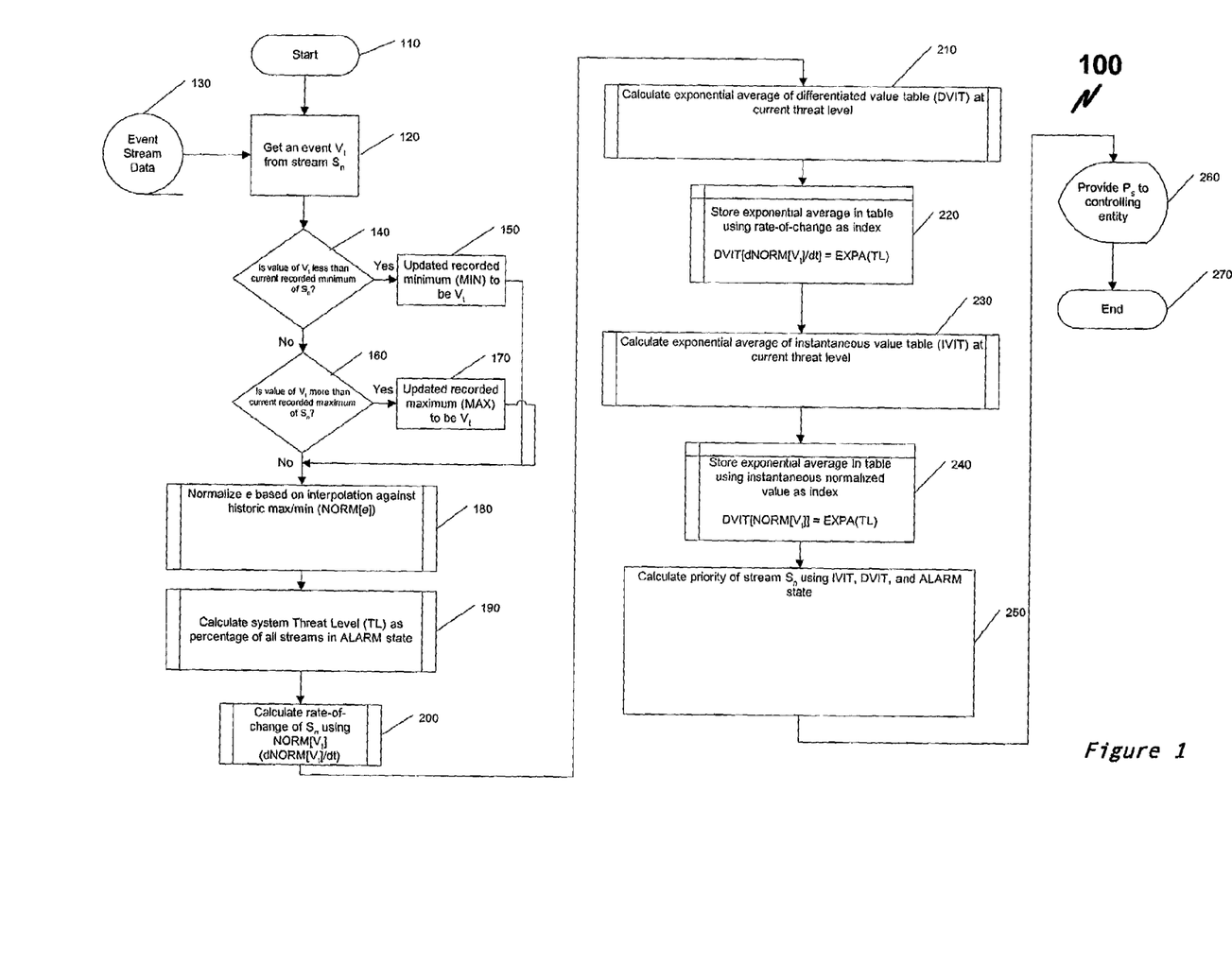
FIG. 1 is a flow diagram illustrating the functions performed by an algorithm in accordance with a preferred form of the present invention.
Figure 2:
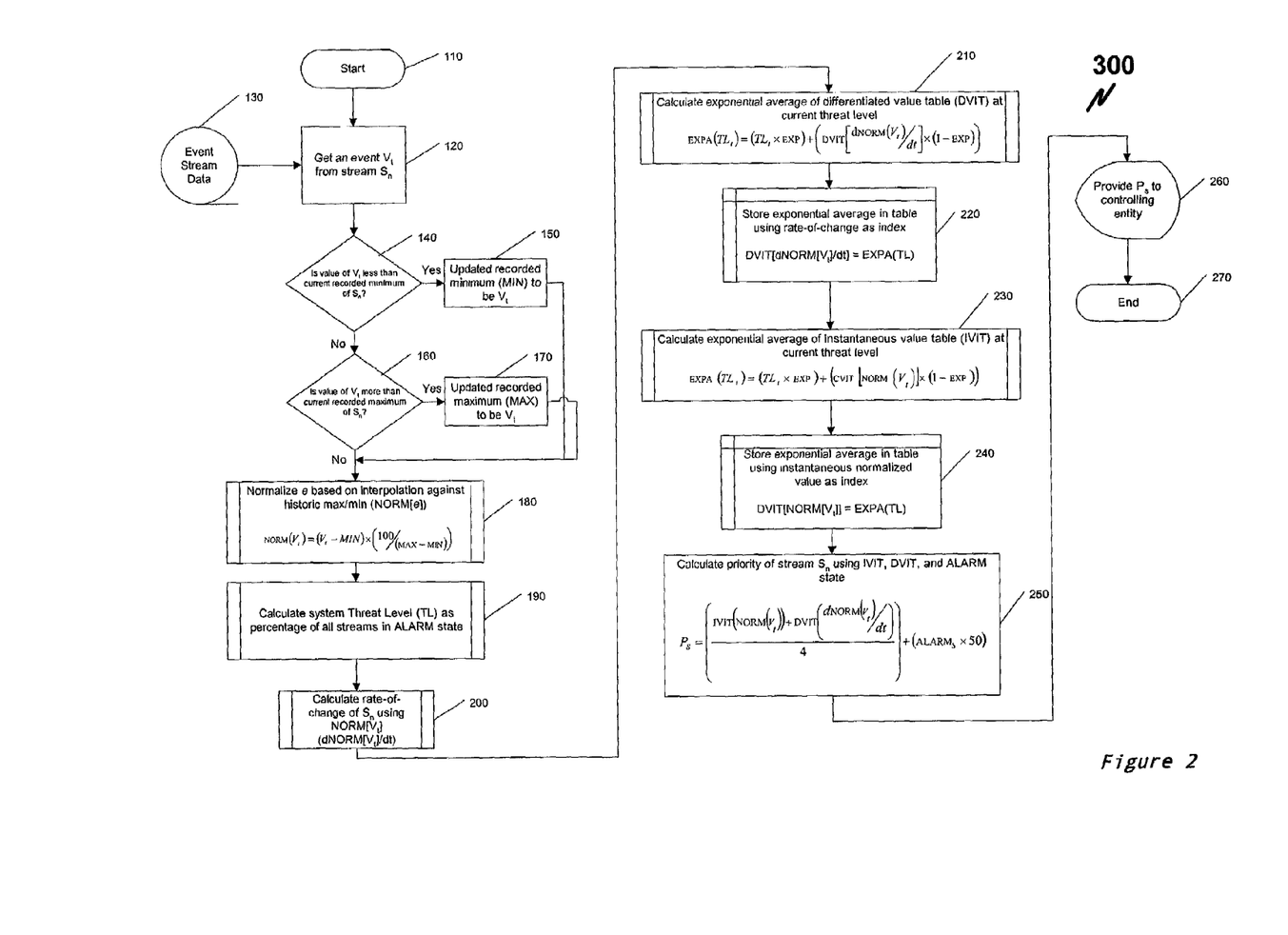
FIG. 2 is an expanded version of the flow diagram shown in FIG. 1.

Turning now to the drawings, FIGS. 1 and 2 illustrate the functions performed by an algorithm 100 in accordance with a preferred form of the present invention. Upon being initialized (step 110), the algorithm 100 will get an event from a selected stream (step 120). Upon receiving the event from the selected stream, the algorithm will determine whether the value of the event is less than a current recorded minimum for the stream (step 140), and if the value is less than the recorded minimum, the algorithm will update the recorded minimum to be the current value (step 150). Next, the algorithm will determine whether the value of the event exceeds a current recorded maximum value for the stream (step 160), and if the value of the event exceeds the recorded maximum, the algorithm will update the recorded maximum to be the current value of the event (step 170). Once the maximum and minimum values for the stream have been updated, or established, the algorithm will normalize the value of the event based upon the currently recorded maximum and minimum values for the stream (step 180).

Following these steps, the algorithm will calculate a system threat level (TL) as, for example, a percentage of all streams in ALARM state (step 190). The algorithm then will calculate a rate of change of the stream values, using the normalized value of the event, and the derivative of the normalized value of the event (step 200).

Next, the algorithm will calculate a first exponential average of the threat level (TL) at time t using historical values obtained from a Differential Value Influence Table (step 210), and the algorithm will store the calculated current exponential average of the threat level (TL) with the Differential Value Influence Table (step 220). The calculation of the first exponential average of the threat level (TL) preferably is performed using the formula set forth in FIG. 2 and reproduced below.

$$EXPA(TL_t) = (TL_t \times EXP) + (DVIT[dNORM(V_t/dt] \times (1 - EXP))$$

Thereafter, the algorithm will calculate a second exponential average of the threat level (TL) using an Instantaneous Value Influence Table (step 230), and the algorithm will store the calculated second exponential average of the threat level (TL) within that table (step 240). The calculation of the second exponential average of the threat level (TL) preferably is performed using the formula set forth in FIG. 2 and reproduced below.

$$EXP_A(TL_t)=(TL_t \times EXP)+(CVIT[NORM(V_t)] \times (1-EXP))$$

Once the above-described, preliminary calculations have been performed, the algorithm will calculate the priority of the event using the first exponential average of the threat level (TL), the second exponential average of the threat level (TL), an alarm status indicator, and if desired, one or more weighting factors (step 250). The equations that preferably are used to perform the prioritization calculation are set forth in FIG. 2 and reproduced below.

$$Ps = \left( \frac{IVIT(NORM(V_t)) + DVIT(dNORM(V_t)/dt)}{4} \right) + (ALARMs \times 50)$$

$$Ps = W_1 \times \left( \frac{W_3 \times IVIT(NORM(V_t)) + W_4 \times DVIT(dNORM(V_t)/dt)}{4} \right) + W_2 \times (ALARMs \times 50)$$

The calculated priority of the event may then be provided to a control circuit, system, or entity (step 260), and the process may be repeated for another event (not shown) or terminated (step 270).

Systems and methods employing an algorithm of the type described above, or an equivalent algorithm, are referred to herein as "historic learning" systems and methods, because of their ability to take historic information into account in performing an event prioritization function, and it is believed that such systems and methods will prove to be quite beneficial to the event management field.

Those skilled in the art will appreciate that systems, methods, and algorithms in accordance with the present invention may have utility in numerous fields. For example, such systems, methods, and algorithms may be used within medical services establishments to monitor and prioritize events in biometric data streams descriptive of patient heart rates, respiratory rates, glucose levels, oxygen perfusion levels, medication rates, temperatures, hemoglobin counts, platelet counts, T cell counts, and the like. And, because such systems, methods, and algorithms have the ability to learn, or to adapt in response to past experiences, those systems, methods, and algorithms may distinguish serious, or non-serious, conditions for each specific patient within a facility using historical data applicable to each individual patient.

Figure 3:
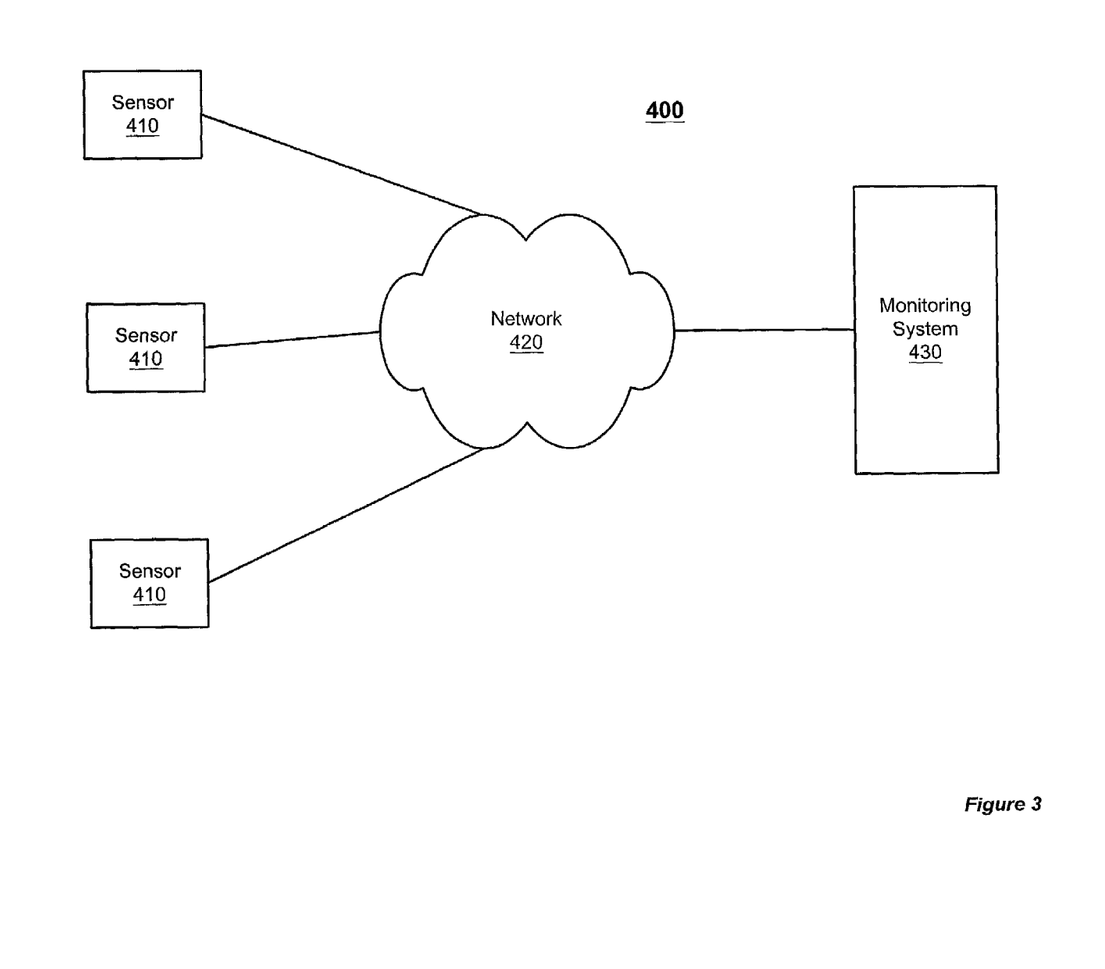
FIG. 3 is a block diagram illustrating a biometric data monitoring system in accordance with a form of the present invention.

Turning now to FIG. 3, in an exemplary medical environment, a biometic parameter monitoring system 400 may comprise a plurality of sensor units 410, such as pulse rate monitors or oxygen perfusion monitors, a network 420 (such as a local area network or direct signal delivery network), and a biometric parameter monitoring system 430 coupled to the network 420. In use, the sensor units 410 will generate a plurality of corresponding data streams Sn (not shown) that will be delivered to the network 420 and, eventually, to the biometric parameter monitoring system 430. The biometric parameter monitoring system 430, which receives the data streams Sn, may utilize a historic learning algorithm of the type described above to prioritize event datum received from the data streams Sn.

It should be appreciated that because an algorithm in accordance with the present invention will evaluate each stream Sn independently, it is possible to utilize several different biometric sensor units 410 within the system 400 described above.

Systems, methods, and algorithms in accordance with the present invention also may have utility in the manufacturing, production, and service distribution fields, because those systems, methods, and algorithms can efficiently identify and give priority to events that may cause substantial disruption to, for example, a manufacturing process or service schedule often well before the full effects of the events are experienced by the system or service provider network. This allows for intervention to occur in a timely fashion and with a higher likelihood of success than would be possible using conventional monitoring and prioritization algorithms.

Figure 4:
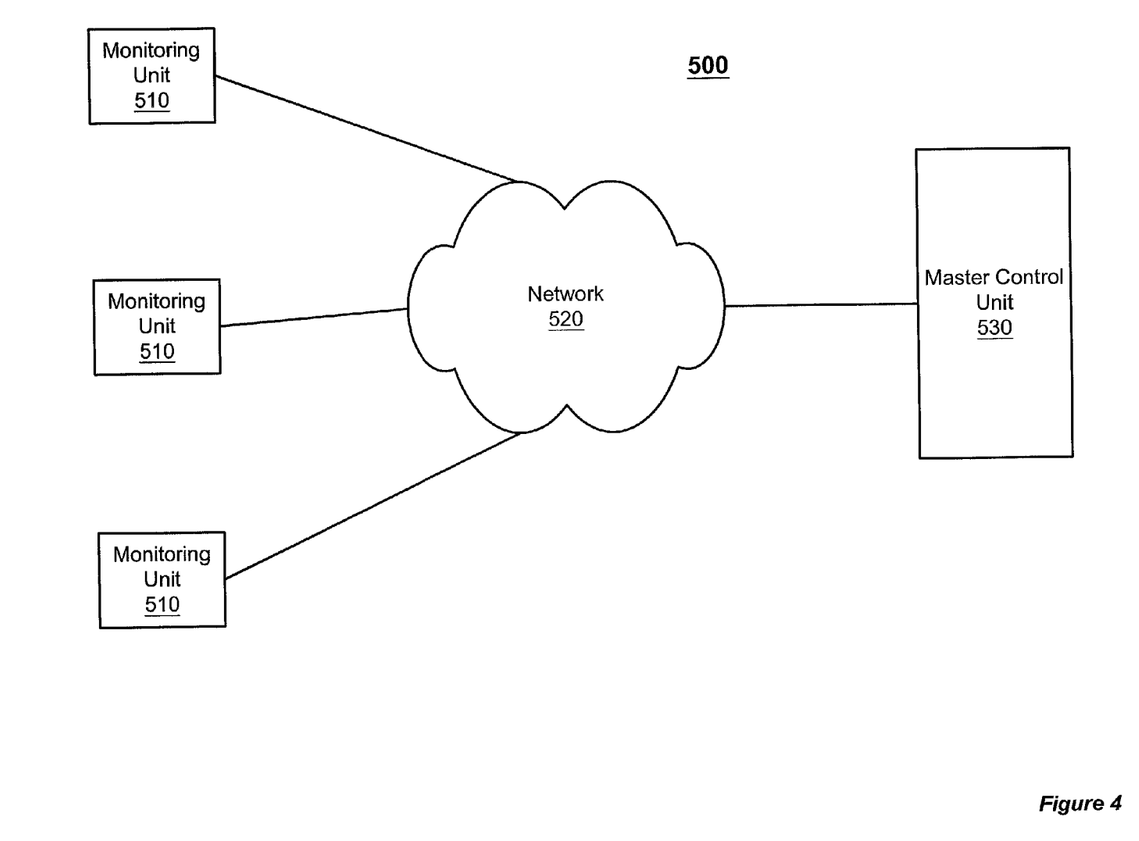
FIG. 4 is a block diagram illustrating a manufacturing process monitoring system in accordance with a form of the present invention.

In one such system 500, shown in FIG. 4, a plurality of process monitoring units 510 may be coupled to via a data communications network 520, such as a local or wide area network, to a process master control unit 530. It will be appreciated that the process monitoring units 510 may, or may not, comprise intelligent units, for monitoring and effecting steps within an overall manufacturing process. In such an embodiment, the master control unit 530, or processing units (not shown) between the process monitoring units 510 and the master control unit 530, may use a historic learning algorithm to prioritize event datum received from streams Sn (not shown) generated by the process monitoring units 510.

It is believed that similar advantages may be obtained by using systems, methods, and algorithms in accordance with the present invention in the information technology (IT) field, as such systems, methods, and algorithms provide IT professionals with a very powerful tool for monitoring, for example, local or wide area network health or storage area network (SAN) health. For example, in an environment where multiple agents collect quantitative metrics about various aspects of an IT system, such as load, performance, available bandwidth, storage capacity, and errors, an algorithm in accordance with the present invention may be used to prioritize events received from the various agents.

Those skilled in the art will appreciate that the systems, methods, and algorithms described herein may be applied to any number of applications where it is important to monitor and prioritize events, and those skilled in the art will appreciate the algorithms and methods described herein may function within virtually any computing environment regardless of the hardware, software, coding languages, protocols, or operating systems that may be employed within those environments.

In this document, the term "computer program product" is used to refer to any media that may be used to provide programming instructions or data to a processing system (not shown), or to any server or processor within the processing system. Examples of such media include any memory products used by or within the system, any storage drives or devices (whether fixed or removable) used by or within the system, and any signals that may be transmitted to, from, or within the system.

Because the invention is susceptible to various modifications and alternative forms, specific examples thereof have been shown in the drawings and are herein described in detail. It should be understood, however, that the invention is not to be limited to the particular forms or methods disclosed, but to the contrary, the invention should encompass all modifications, alternatives, and equivalents falling within the spirit and scope of the appended claims.

What is claimed is:

1. A method for prioritizing event datum received from a plurality of asynchronous telemetric streams within a system, the method comprising:
   receiving an event from one of the streams;
   determining whether a value of the event is less than a previously recorded minimum value for the stream, and if the value of the event is less than the previously recorded minimum value, updating the recorded minimum value to the value of the event;
   determining whether the value of the event is greater than a previously recorded maximum value for the stream, and if the value of the event is greater than the previously recorded, updating the recorded maximum value to the value of the event;
   generating a normalized event value based upon the value of the event, the recorded minimum value, and the recorded maximum value; determining a system threat level as a percentage of the streams that exhibit an alarm state;
   calculating a normalized rate of change of the stream;
   calculating a first exponential average based upon the determined threat level and a threat level previously stored in a first table providing a correlation between system threat levels and normalized event values;
   calculating a second exponential average based upon the determined threat level and a threat level previously stored in a second table providing a correlation between system threat levels and normalized stream rates of change; and
   calculating a priority of the stream based upon a predetermined relationship between the first exponential average, the second exponential average, and an alarm status indicator associated with the stream.

2. The method of claim 1, wherein
   the first exponential average comprises a number in a range from 0 to 100, the second exponential average comprises a number in a range from 0 to 100, and the alarm status indicator comprises either 1 or 0; and
   calculating a priority of the stream comprises dividing the sum of the first exponential average and second exponential average by 4 and adding to a resulting value a product of the alarm status indicator and 50.

3. The method of claim 1, wherein the predetermined relationship between the first exponential average, the second exponential average, and the alarm status indicator provides for predetermined weightings of the first exponential average, the second exponential average, and the alarm status indicator.

4. A method for prioritizing event datum received from a plurality of streams within a system, the method comprising:
   receiving an event value from a stream;
   generating a normalized event value based upon the received event value;
   calculating a normalized rate of change of the stream;
   determining a system threat level based upon a number of alarm status indications associated with the plurality of streams;
   calculating a first exponential average based upon the determined threat level and a threat level previously stored in a first table providing a correlation between system threat levels and normalized event values;
   calculating a second exponential average based upon the determined threat level and a threat level previously stored in a second table providing a correlation between system threat levels and normalized stream rates of change; and
   calculating a priority of the stream based upon a predetermined relationship between the first exponential average, the second exponential average, and an alarm status indicator associated with the stream.

5. A method for prioritizing event datum received from a plurality of streams within a system, the method comprising:
   receiving an event from one of the streams; determining a current state of system health;
   generating a current normalized event value and a current normalized stream rate of change value; and
   defining a priority for the stream based upon a predetermined relationship between the current state of system health, the current normalized event value, the current normalized stream rate of change value, previously stored normalized event values, previously stored stream rate of change values, and an alarm status indicator associated with the stream.

6. The method of claim 5 wherein defining a priority further comprises:
   calculating a first exponential average based upon the current state of system health and a state of system health previously stored in a first table providing a correlation between system health and normalized event values;
   calculating a second exponential average based upon the current state of system health and a state of system health previously stored in a second table providing a correlation between system threat levels and normalized stream rates of change; and
   calculating a priority of the stream based upon a predetermined relationship between the first exponential average, the second exponential average, and the alarm status indicator associated with the stream.

7. The method of claim 6, wherein
   the first exponential average comprises a number in a range from 0 to 100, the second exponential average comprises a number in a range from 0 to 100, and the alarm status indicator comprises either 1 or 0; and
   the calculating a priority of the stream comprises dividing the sum of the first exponential average and second exponential average by 4 and adding to a resulting value a product of the alarm status indicator and 50.

8. A computer program product in computer readable medium for use in an event monitoring system, the computer program product comprising instructions that, when executed by a processor, cause the processor to:
   get an event from a stream selected from a plurality of streams;
   determine a current normalized event value and a current normalized rate of change of event values for the stream;
   determine a level of current system health;
   evaluate a historic relationship between levels of system health, normalized event values for the stream, and normalized rates of change of event values for the stream;
   predict an effect upon system health that is likely to occur based upon the determined current normalized event value for the stream, the determined current normalized rate of change of event values for the stream, and the evaluated historic relationship; and determine a priority for the event based upon the predicted effect.

9. An event prioritization system for using in monitoring a plurality of data streams generated by a communications network, the event prioritization system comprising:
   a plurality of agent applications for monitoring selected parameters descriptive of a functionality of the communications network, each such agent generating an independent data stream and delivering the generated stream to a common nexus, and a processor associated with the common nexus, the processor being configured to execute a historic learning algorithm to assign priorities to event datum received from the data streams generated by the agents, wherein the processor executes a set of programming instructions for causing the processor to receive an event from one of the streams;

determine whether a value of the event is less than a previously recorded minimum value for the stream, and if the value of the event is less than the previously recorded minimum value, update the recorded minimum value to the value of the event;

determine whether the value of the event is greater than a previously recorded maximum value for the stream, and if the value of the event is greater than the previously recorded, update the recorded minimum value to the value of the event;

generate a normalized event value based upon the value of the event, the recorded minimum value, and the recorded maximum value;

determine a system threat level as a percentage of the streams that exhibit an alarm state;

calculate a normalized rate of change of the stream;

calculate a first exponential average based upon the determined threat level and a threat level previously stored in a first table providing a correlation between system threat levels and normalized event values;

calculate a second exponential average based upon the determined threat level and a threat level previously stored in a second table providing a correlation between system threat levels and normalized stream rates of change; and calculate a priority of the stream based upon a predetermined relationship between the first exponential average, the second exponential average, and an alarm status indicator associated with the stream.

* * * * *